(12) United States Patent
Behnke

(10) Patent No.: US 8,747,398 B2
(45) Date of Patent: Jun. 10, 2014

(54) FREQUENCY TUNING IN A MICROWAVE ELECTROSURGICAL SYSTEM

(75) Inventor: Robert Behnke, Erie, CO (US)

(73) Assignee: Covidien LP, Mansfield, MA (US)

( * ) Notice: Subject to any disclaimer, the term of this patent is extended or adjusted under 35 U.S.C. 154(b) by 1592 days.

(21) Appl. No.: 11/900,874

(22) Filed: Sep. 13, 2007

(65) Prior Publication Data

US 2009/0076492 A1 Mar. 19, 2009

(51) Int. Cl.
*A61B 18/18* (2006.01)

(52) U.S. Cl.
USPC .......................................................... 606/33

(58) Field of Classification Search
USPC ........... 606/32–34, 41–42; 600/9–11; 333/32; 343/861–862
See application file for complete search history.

(56) References Cited

U.S. PATENT DOCUMENTS

| | | |
|---|---|---|
| 1,995,526 A | 3/1935 | Wappler |
| 4,204,549 A | 5/1980 | Paglione |
| 4,228,809 A | 10/1980 | Paglione |
| 4,311,154 A | 1/1982 | Sterzer et al. |
| 4,375,220 A | 3/1983 | Matvias |
| 4,494,539 A | 1/1985 | Zenitani et al. |
| 4,534,347 A | 8/1985 | Taylor |
| 4,580,557 A | 4/1986 | Hertzmann |
| 4,612,940 A | 9/1986 | Kasevich et al. |
| 4,632,127 A | 12/1986 | Sterzer |
| 4,632,128 A | 12/1986 | Paglione et al. |
| 4,638,436 A | 1/1987 | Badger et al. |
| 4,657,015 A | 4/1987 | Irnich |
| 4,672,980 A | 6/1987 | Turner |
| 4,741,348 A | 5/1988 | Kikuchi et al. |
| 4,744,372 A | 5/1988 | Kikuchi et al. |
| 4,747,416 A | 5/1988 | Kikuchi et al. |
| 4,753,248 A | 6/1988 | Engler et al. |
| 4,799,034 A * | 1/1989 | Silverman et al. ............ 333/202 |
| 4,815,479 A | 3/1989 | Carr |
| 4,860,752 A | 8/1989 | Turner |
| 4,860,770 A | 8/1989 | Kikuchi et al. |
| 4,873,995 A | 10/1989 | Kikuchi et al. |
| 4,884,580 A | 12/1989 | Kikuchi et al. |
| 4,945,912 A | 8/1990 | Langberg |
| 4,955,377 A | 9/1990 | Lennox et al. |
| 4,967,765 A | 11/1990 | Turner et al. |
| 5,019,076 A | 5/1991 | Yamanashi et al. |
| 5,025,810 A | 6/1991 | Kikuchi et al. |
| 5,033,478 A | 7/1991 | Kikuchi et al. |
| 5,057,106 A | 10/1991 | Kasevich et al. |

(Continued)

FOREIGN PATENT DOCUMENTS

WO WO 97/35639 A1 10/1997

OTHER PUBLICATIONS

European Search Report, Application No. EP 2 036 512 A1 dated Nov. 27, 2008.

(Continued)

*Primary Examiner* — Ronald Hupczey, Jr.

(57) ABSTRACT

A method and apparatus is disclosed for the ablation of biological tissue to produce a therapeutic effect. An adjustment is made to the output frequency of an electrosurgical generator during the ablation cycle to accommodate changes in the electrical properties of the apparatus and the biological tissues that occur as energy is transferred to the tissue. The adjustment is made to better align the source impedance with that of the load.

13 Claims, 4 Drawing Sheets

(56) References Cited

U.S. PATENT DOCUMENTS

| | | |
|---|---|---|
| 5,148,814 A | 9/1992 | Kikuchi et al. |
| 5,188,122 A | 2/1993 | Phipps et al. |
| 5,211,570 A | 5/1993 | Bitney |
| 5,220,927 A | 6/1993 | Astrahan et al. |
| 5,234,004 A | 8/1993 | Hascoet et al. |
| 5,249,585 A | 10/1993 | Turner et al. |
| 5,275,597 A | 1/1994 | Higgins et al. |
| 5,295,955 A | 3/1994 | Rosen et al. |
| 5,330,518 A | 7/1994 | Neilson et al. |
| 5,342,349 A | 8/1994 | Kaufman |
| 5,344,435 A | 9/1994 | Turner et al. |
| 5,354,325 A | 10/1994 | Chive et al. |
| 5,364,392 A | 11/1994 | Warner et al. |
| 5,383,874 A | 1/1995 | Jackson et al. |
| 5,405,346 A | 4/1995 | Grundy et al. |
| 5,433,740 A | 7/1995 | Yamaguchi |
| 5,571,098 A | 11/1996 | Domankevitz et al. |
| 5,571,154 A | 11/1996 | Ren |
| 5,584,830 A | 12/1996 | Ladd et al. |
| 5,620,480 A | 4/1997 | Rudie |
| 5,628,771 A | 5/1997 | Mizukawa et al. |
| 5,693,082 A | 12/1997 | Warner et al. |
| 5,800,494 A | 9/1998 | Campbell et al. |
| 5,836,943 A | 11/1998 | Miller, III |
| 5,904,709 A | 5/1999 | Arndt et al. |
| 5,922,013 A | 7/1999 | Fallik |
| 5,938,692 A * | 8/1999 | Rudie ............ 607/101 |
| 5,944,022 A | 8/1999 | Nardella et al. |
| 5,957,969 A * | 9/1999 | Warner et al. ........ 607/156 |
| 5,961,871 A | 10/1999 | Bible et al. |
| 5,967,976 A | 10/1999 | Larsen et al. |
| 6,016,452 A | 1/2000 | Kasevich |
| 6,019,757 A | 2/2000 | Scheldrup |
| 6,022,346 A | 2/2000 | Panescu et al. |
| 6,032,078 A | 2/2000 | Rudie |
| 6,047,216 A | 4/2000 | Carl et al. |
| 6,067,475 A * | 5/2000 | Graves et al. ........ 607/101 |
| 6,068,627 A | 5/2000 | Orszulak et al. |
| 6,093,028 A | 7/2000 | Yang |
| 6,097,985 A | 8/2000 | Kasevich et al. |
| 6,106,520 A | 8/2000 | Laufer et al. |
| 6,122,551 A | 9/2000 | Rudie et al. |
| 6,134,476 A | 10/2000 | Arndt et al. |
| 6,136,020 A | 10/2000 | Faour |
| 6,161,048 A | 12/2000 | Sluijter et al. |
| 6,163,726 A | 12/2000 | Wolf |
| 6,167,313 A | 12/2000 | Gray et al. |
| 6,175,768 B1 | 1/2001 | Arndt et al. |
| 6,179,832 B1 | 1/2001 | Jones et al. |
| 6,181,970 B1 | 1/2001 | Kasevich |
| 6,188,930 B1 | 2/2001 | Carson |
| 6,216,703 B1 | 4/2001 | Manker et al. |
| 6,226,553 B1 | 5/2001 | Carl et al. |
| 6,228,079 B1 | 5/2001 | Koenig |
| 6,233,490 B1 | 5/2001 | Kasevich |
| 6,246,912 B1 | 6/2001 | Sluijter et al. |
| 6,251,128 B1 | 6/2001 | Knopp et al. |
| 6,272,384 B1 | 8/2001 | Simon et al. |
| 6,273,886 B1 | 8/2001 | Edwards et al. |
| 6,275,738 B1 | 8/2001 | Kasevich et al. |
| 6,289,249 B1 | 9/2001 | Arndt et al. |
| 6,293,941 B1 | 9/2001 | Strul et al. |
| 6,312,391 B1 | 11/2001 | Ramadhyani et al. |
| 6,325,799 B1 | 12/2001 | Goble |
| 6,334,074 B1 | 12/2001 | Spertell |
| 6,347,251 B1 | 2/2002 | Deng |
| 6,366,818 B1 | 4/2002 | Bolmsjo |
| 6,380,815 B1 | 4/2002 | Fehrenbach et al. |
| 6,383,183 B1 | 5/2002 | Sekino et al. |
| 6,402,742 B1 | 6/2002 | Blewett et al. |
| 6,430,446 B1 | 8/2002 | Knowlton |
| 6,451,015 B1 | 9/2002 | Rittman, III et al. |
| 6,470,217 B1 | 10/2002 | Fenn et al. |
| 6,477,426 B1 | 11/2002 | Fenn et al. |
| 6,485,486 B1 | 11/2002 | Trembly et al. |
| 6,490,488 B1 | 12/2002 | Rudie et al. |
| 6,494,880 B1 | 12/2002 | Swanson et al. |
| 6,496,736 B1 | 12/2002 | Carl et al. |
| 6,496,738 B2 | 12/2002 | Carr |
| 6,503,191 B1 | 1/2003 | Miller |
| 6,512,956 B2 | 1/2003 | Arndt et al. |
| 6,522,931 B2 | 2/2003 | Manker et al. |
| 6,526,320 B2 | 2/2003 | Mitchell |
| 6,542,767 B1 | 4/2003 | McNichols et al. |
| 6,544,069 B1 | 4/2003 | Enriquez et al. |
| 6,582,425 B2 | 6/2003 | Simpson |
| 6,582,427 B1 | 6/2003 | Goble et al. |
| 6,592,579 B2 | 7/2003 | Arndt et al. |
| 6,628,990 B1 | 9/2003 | Habib et al. |
| 6,640,139 B1 | 10/2003 | Ueberle |
| 6,666,862 B2 | 12/2003 | Jain et al. |
| 6,671,535 B1 | 12/2003 | McNichols et al. |
| 6,675,050 B2 | 1/2004 | Arndt et al. |
| 6,685,701 B2 | 2/2004 | Orszulak et al. |
| 6,689,131 B2 | 2/2004 | McClurken |
| 6,690,976 B2 | 2/2004 | Fenn et al. |
| 6,723,091 B2 | 4/2004 | Goble et al. |
| 6,725,095 B2 | 4/2004 | Fenn et al. |
| 6,743,225 B2 | 6/2004 | Sanchez et al. |
| 6,752,804 B2 | 6/2004 | Simpson et al. |
| 6,771,139 B2 | 8/2004 | Schultheiss et al. |
| 6,788,977 B2 | 9/2004 | Fenn et al. |
| 6,790,206 B2 | 9/2004 | Panescu |
| 6,796,980 B2 | 9/2004 | Hall |
| 6,823,218 B2 | 11/2004 | Berube |
| 6,847,848 B2 | 1/2005 | Sterzer et al. |
| 6,866,624 B2 | 3/2005 | Chornenky et al. |
| 6,939,348 B2 | 9/2005 | Malecki et al. |
| 6,944,504 B1 | 9/2005 | Arndt et al. |
| 6,955,675 B2 | 10/2005 | Jain |
| 6,957,108 B2 | 10/2005 | Turner et al. |
| 6,962,586 B2 | 11/2005 | Berube et al. |
| 6,974,463 B2 | 12/2005 | Magers et al. |
| 6,986,764 B2 | 1/2006 | Davenport et al. |
| 6,986,770 B2 | 1/2006 | Hood |
| 6,994,704 B2 | 2/2006 | Qin et al. |
| 7,041,096 B2 | 5/2006 | Malis et al. |
| 7,066,933 B2 | 6/2006 | Hagg |
| 7,070,595 B2 | 7/2006 | Ormsby et al. |
| 7,089,064 B2 | 8/2006 | Manker et al. |
| 7,093,601 B2 | 8/2006 | Manker et al. |
| 7,105,011 B2 | 9/2006 | Auge, II |
| 7,113,832 B2 | 9/2006 | Longo |
| 7,115,121 B2 | 10/2006 | Novak |
| 7,115,126 B2 | 10/2006 | Berube et al. |
| 7,122,031 B2 | 10/2006 | Edwards et al. |
| 7,131,445 B2 | 11/2006 | Amoah |
| 7,169,144 B2 | 1/2007 | Hoey et al. |
| 7,194,297 B2 | 3/2007 | Talpade et al. |
| 7,195,627 B2 | 3/2007 | Amoah et al. |
| 7,197,363 B2 | 3/2007 | Prakash et al. |
| 7,200,445 B1 | 4/2007 | Dalbee et al. |
| 7,202,747 B2 | 4/2007 | Forse et al. |
| 7,203,556 B2 | 4/2007 | Daners |
| 7,211,081 B2 | 5/2007 | Goble |
| 7,214,224 B2 | 5/2007 | Goble |
| 7,220,260 B2 | 5/2007 | Fleming et al. |
| 7,226,447 B2 | 6/2007 | Uchida et al. |
| 7,594,913 B2 * | 9/2009 | Ormsby et al. ........ 606/33 |
| 2001/0008966 A1 | 7/2001 | Arndt et al. |
| 2001/0016762 A1 | 8/2001 | Carr |
| 2001/0020178 A1 | 9/2001 | Arndt et al. |
| 2002/0000234 A1 | 1/2002 | Manker et al. |
| 2002/0165529 A1 | 11/2002 | Danek |
| 2002/0193849 A1 | 12/2002 | Fenn et al. |
| 2003/0014043 A1 | 1/2003 | Henry et al. |
| 2003/0023238 A1 | 1/2003 | Manker et al. |
| 2003/0055471 A1 | 3/2003 | Fenn et al. |
| 2003/0065317 A1 | 4/2003 | Rudie et al. |
| 2003/0069619 A1 | 4/2003 | Fenn et al. |
| 2003/0144655 A1 | 7/2003 | Panescu |
| 2003/0191513 A1 | 10/2003 | Manker et al. |
| 2003/0199863 A1 | 10/2003 | Swanson et al. |
| 2004/0032301 A1 | 2/2004 | Schultheiss et al. |

(56) References Cited

U.S. PATENT DOCUMENTS

| | | |
|---|---|---|
| 2004/0049254 A1 | 3/2004 | Longo |
| 2004/0122420 A1 | 6/2004 | Amoah |
| 2004/0133254 A1 | 7/2004 | Sterzer et al. |
| 2004/0193147 A1 | 9/2004 | Malecki et al. |
| 2004/0215179 A1 | 10/2004 | Swoyer et al. |
| 2004/0215182 A1 | 10/2004 | Lee |
| 2004/0243120 A1 | 12/2004 | Orszulak et al. |
| 2004/0243200 A1 | 12/2004 | Turner et al. |
| 2005/0038419 A9 | 2/2005 | Arnold et al. |
| 2005/0137662 A1 | 6/2005 | Morris et al. |
| 2005/0143795 A1 | 6/2005 | Habib et al. |
| 2005/0149010 A1 | 7/2005 | Turovskiy et al. |
| 2005/0149012 A1 | 7/2005 | Penny et al. |
| 2005/0182393 A1 | 8/2005 | Abboud et al. |
| 2005/0184922 A1 * | 8/2005 | Ida et al. ............... 343/861 |
| 2005/0228370 A1 | 10/2005 | Sterzer et al. |
| 2005/0240239 A1 | 10/2005 | Boveja et al. |
| 2005/0245920 A1 | 11/2005 | Vitullo et al. |
| 2006/0004351 A1 | 1/2006 | Arless et al. |
| 2006/0015161 A1 | 1/2006 | Longo et al. |
| 2006/0015162 A1 | 1/2006 | Edward et al. |
| 2006/0030914 A1 | 2/2006 | Eggers et al. |
| 2006/0106375 A1 | 5/2006 | Werneth et al. |
| 2006/0116673 A1 | 6/2006 | Gauthier et al. |
| 2006/0142753 A1 | 6/2006 | Francischelli et al. |
| 2006/0287649 A1 | 12/2006 | Ormsby |

OTHER PUBLICATIONS

European Search Report for European Patent Appln. No. 08015842.1 dated Jan. Oct. 1, 2010.

* cited by examiner

*FIG. 3C*  *FIG. 3D*

FREQUENCY TUNING IN A MICROWAVE ELECTROSURGICAL SYSTEM

BACKGROUND

1. Technical Field

The present disclosure relates to a system and related methods for employing electromagnetic energy in the microwave frequencies to produce a therapeutic effect on targeted tissue at a surgical site. In particular, the present disclosure relates to systems and methods of impedance matching to maximize energy delivered to target tissue.

2. Background of Related Art

Electromagnetic radiation may be used to heat cells to produce a therapeutic effect. For example, microwave energy has been used to selectively ablate certain types of cancerous cells found to denature at elevated temperatures slightly lower than temperatures normally injurious to healthy cells. Destroying cellular tissue in place may be less traumatic than removing it in a conventional surgery. Accordingly, a microwave ablation procedure may be an attractive option for many patients who are not good candidates for conventional surgery.

To denature many malignant growths of cells, temperatures above about 41.5° C. should be achieved. However, because thermal damage to most normal types of cells is commonly observed at temperatures above about 43° C., caution must be taken not to exceed this value. While it is true that electromagnetic energy used in ablative treatments is rapidly dissipated to non-destructive levels by natural processes such as conduction and convection due to circulating fluids, the temperature range suitable for ablative treatment is small, so great care must be taken in the application of microwave energy.

In a typical microwave ablation procedure, an antenna is positioned in the proximity of the tissue to be treated. For precise control, the antenna may be positioned directly inside the targeted tissue. A generator produces an electromagnetic oscillation, which may be transmitted over a coaxial transmission line to the antenna at its distal end. An electromagnetic field created by the antenna causes friction at a molecular level resulting in elevated temperatures in the vicinity thereof.

One concern in the management of microwave energy is impedance matching. In order to maximize the power transferred from a source to a load, the output impedance of the source should equal the input impedance of the load. Failure to match impedances may result in standing waves on the transmission line due to reflections of the incident power. In the case of microwave tissue ablation, the source is often configured with impedance throughout the appropriate frequency range approximately equal to that of the load to be ablated, which for most human tissue is approximately 50 ohms. However, as the target tissue is ablated, heating of the transmission line components and changes in the electrical properties of the target tissue tend to vary the load impedance over time. When the load impedances change, a greater portion of the power is reflected and the performance of the antenna system is diminished.

SUMMARY

In light of the foregoing, a need exists for ablation systems and methods not only for preliminarily matching source impedances to load impedances, but also for accommodating changing tissue impedances occurring during the ablation procedure. In one embodiment, a microwave antenna is positioned in close proximity to a targeted tissue. Microwave energy is delivered to the antenna at a particular frequency through a transmission line, and a power signal reflected by the targeted tissue is measured. The particular frequency of the microwave energy is adjusted to reduce the energy reflected. A trocar may be used to position the antenna through the skin of a patient, and an initial frequency adjustment may be made to effect a source impedance to about 50 ohms. An output power may be adjusted in combination with the frequency adjustment. The reflected power signal measured may be compared to a predetermined threshold and frequency adjustments may made only when the reflected power signal exceeds the threshold value.

In another embodiment, a system for tissue ablation includes a microwave antenna configured for direct insertion into targeted tissue, a generator of microwave energy including a means for adjusting a frequency operatively connected to the antenna by a transmission line, a monitor operatively connected to the transmission line capable of sampling or measuring a reflected signal, and a means of communicating information concerning the reflected power to the generator. The monitor may include a dual directional coupler configured to sample at least one of the reflected signal and a forward signal. The means of communicating the reflected power information may include a visual display on an amplifier configured to amplify a signal output by a generator.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIGS. 3B through 3D represent a simplified impedance matching circuit;

DETAILED DESCRIPTION OF EMBODIMENTS

Figure 1:
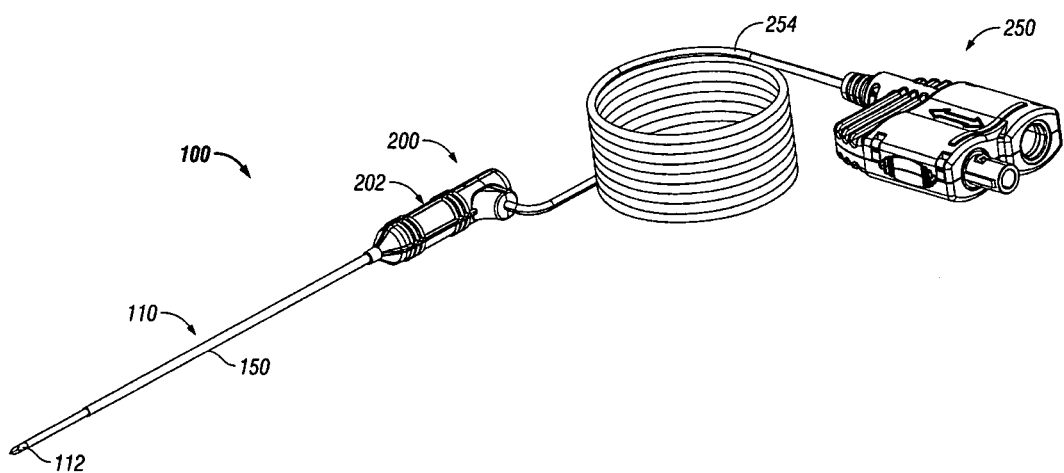
FIG. 1 is a perspective view of an exemplary embodiment of a microwave probe assembly.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

The exemplary embodiments of the apparatus disclosed herein are discussed in terms of performing a diagnostic or therapeutic procedure involving collecting or delivering electrical signals relative to a subject. Such procedures are inclusive of, but, not limited to microwave tissue ablation and related treatments of diseases and body ailments of a subject. In the discussion that follows, the term "clinician" refers to a doctor, nurse, or other care provider and may include support personnel.

Referring initially to FIG. 1, an exemplary microwave probe assembly 100 includes a microwave probe 110, a handle assembly 200, an electrical hub 250 and an electrical cable 254. Microwave probe 110 includes an outer jacket 150 and a sharpened trocar tip 112 shaped to permit penetration of skin and intermediate tissue to allow a radiating antenna portion of microwave probe 110 to be positioned adjacent targeted biological tissue. Handle assembly 200 includes a housing 202 adapted to be grasped by a hand of a clinician to handle probe 110. Electrical cable 254 may be a coaxial cable and together with hub 250 is configured to connect the microwave probe assembly 100 to a source of microwave energy, for example an electrosurgical microwave generator 420 (see FIG. 4).

Figure 2:
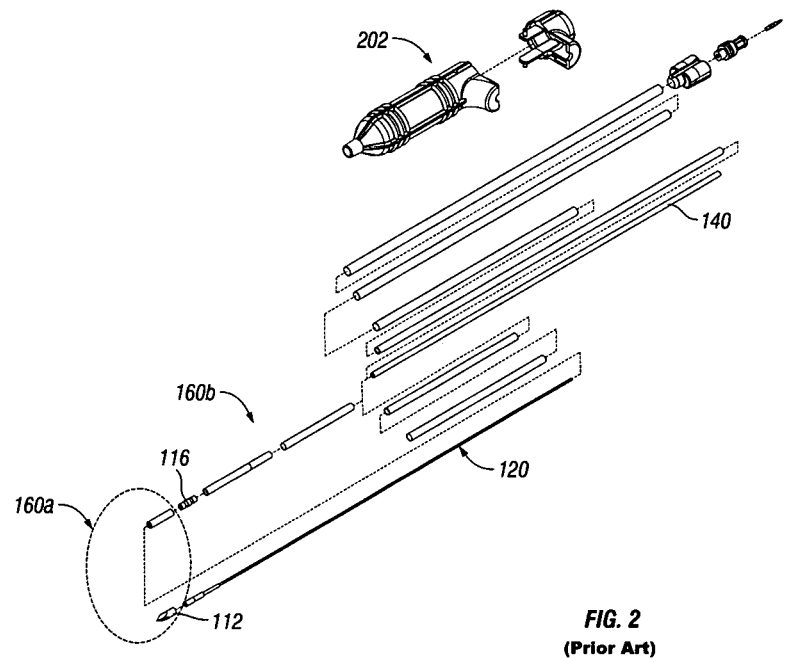
FIG. 2 is a perspective view with parts separated of the probe depicted in FIG. 1.

As seen in FIG. 2, the microwave probe 110 includes an inner conductor 120 and an outer conductor 140 to supply energy to a distal radiating portion 160a and a proximal radiating portion 160b respectively. A dielectric puck 116 separates the radiating portions 160a, 160b such that an opposite charge imparted on the radiating portions 160a, 160b establishes a magnetic field between them. Reference may be made to U.S. patent application Ser. No. 10/482,362, filed on Jul. 20, 2004, for a detailed discussion of the construction and operation of the microwave probe assembly 100.

Figure 3A:
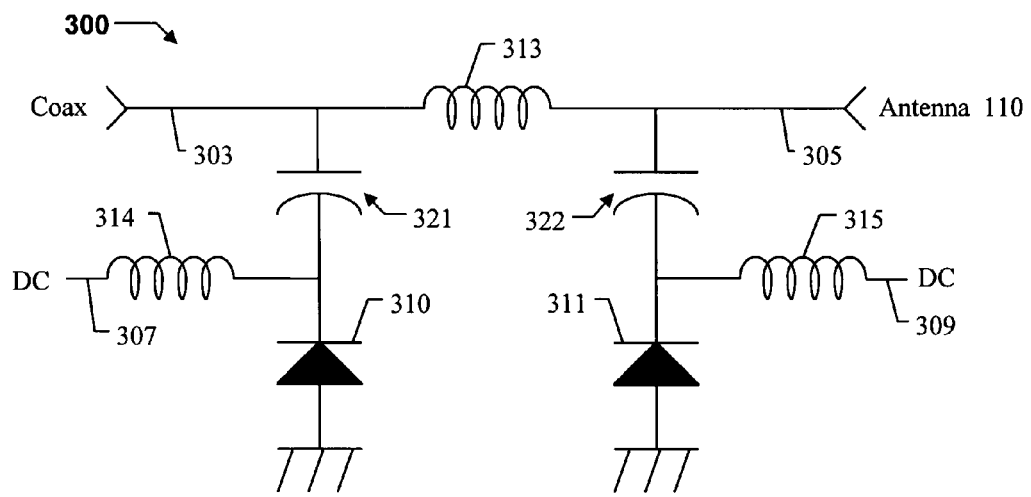
FIG. 3A is a schematic diagram of an impedance matching circuit of the microwave ablation system of the present disclosure.

In accordance with the present disclosure, one method of matching the impedance of the antenna 110 to the source impedance is referred to as "active matching." Such a method may require coupling additional electrical components to the microwave probe assembly 100 to electrically communicate with inner and outer conductors 120, 140. As seen in FIG. 3A, an active matching control circuit is generally designated as 300.

Active matching control circuit 300 includes an input line 303 for receiving an output signal or energy from microwave generator 420 (FIG. 4), and an output line 305 for transmitting an impedance matched output signal or energy to microwave probe or antenna 110. Control circuit 300 further includes an inductor 313 electrically connected in series between input line 303 and output line 305. Control circuit 300 includes a first capacitor 321 and a first tuning diode 310 electrically connected in series to one another and connected in parallel to input line 303 at a location upstream of inductor 313; and a second capacitor 322 and a second tuning diode 311 electrically connected in series to one another and connected to output line 305 at a location downstream of inductor 313. Control circuit 300 also includes a first inductor 314 connected to a direct current ("DC") source via supply line 307 and is connected at a point between first capacitor 321 and first tuning diode 310. Control circuit 300 further includes a second inductor 315 connected to a "DC" source via a supply line 309 and is connected at a point between second capacitor 322 and the second tuning diode 311.

In operation, in order to match the impedance of the load on output line 305 to that of microwave probe 110, tuning diodes 310, 311 may be adjusted as needed or desired. PIN and/or varactor diodes 310, 311 may be used such that when a "DC" voltage is applied on supply lines 307, 309, the capacitance exhibited by diodes 310, 311 will vary in accordance with the applied voltage thereto. Inductors 314, 315 are selected to have high impedances over an appropriate range of frequencies so that inductors 314, 315 act as RF chokes, thereby keeping "DC" supply lines 307, 309 free from the alternating current supplied to output line 305. When diodes 310, 311 are appropriately tuned, capacitors 321, 322 and inductor 313 may compensate for a difference in impedance between the system and the tissue. Active matching control circuit 300 is placed as close as possible to the radiating portions 160a, 160b to minimize losses therebetween.

Figure 3B:
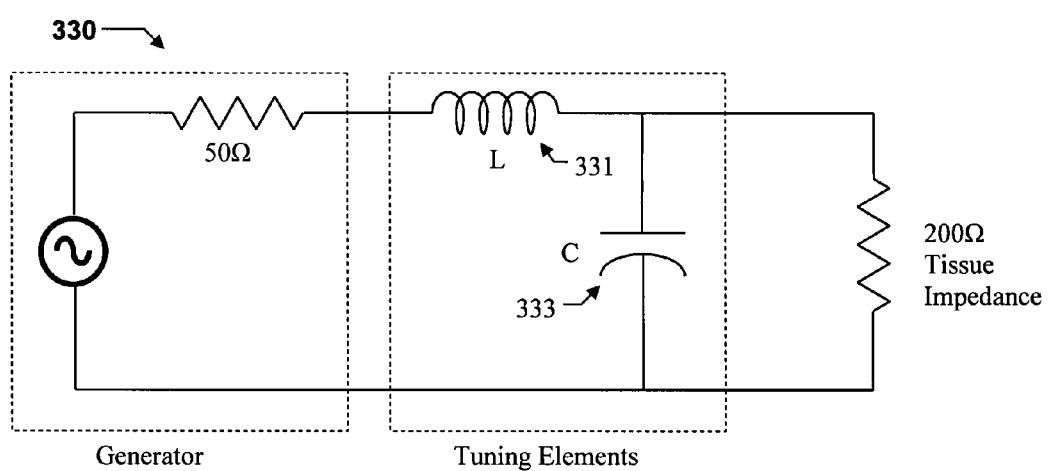

A simplified example of such tuning is described below with reference to FIGS. 3B through 3D. As seen in FIG. 3B, at some time after initiating a tissue ablation procedure, the tissue impedance has risen to 200 ohms creating a substantial mismatch with the 50 ohm generator 330. While the fixed inductor 331 may have an inductance value of 15 nH, the variable capacitor 333 may be tuned as described above to have a capacitance of 1.5 pf. For a predetermined frequency of 915 MHz supplied by the generator 330, this yields the inductive and capacitive reactance values of:

$$x_L = j86.6\Omega \; x_C = -j116\Omega$$

Now rotating the 200 ohm tissue impedance through the matching network, the tissue is in parallel with the 1.5 pf capacitor. First equivalent impedance $Z_{L1}$ may be calculated using the parallel impedance formula.

$$Z_{L1} = \frac{(200\Omega) \cdot (-j116\Omega)}{200\Omega - j116\Omega} \cong (50 - j86.8)\Omega$$

Representing the tissue load and variable capacitor with the first equivalent impedance yields the circuit depicted in FIG. 3C. It can be seen that a second equivalent impedance $Z_{L2}$ may now be calculated for the fixed inductor and the first equivalent impedance in series.

$$Z_{L2} = (50 - j86.8)\Omega + j86.6\Omega \cong 50\Omega$$

Second equivalent impedance $Z_{L2}$ may be calculated and represented in the circuit depicted in FIG. 3D. It can be seen that the second equivalent impedance is substantially matched to the generator impedance. Thus, appropriately tuning the variable capacitor allows for maximum power delivery to the tissue load.

Figure 4:
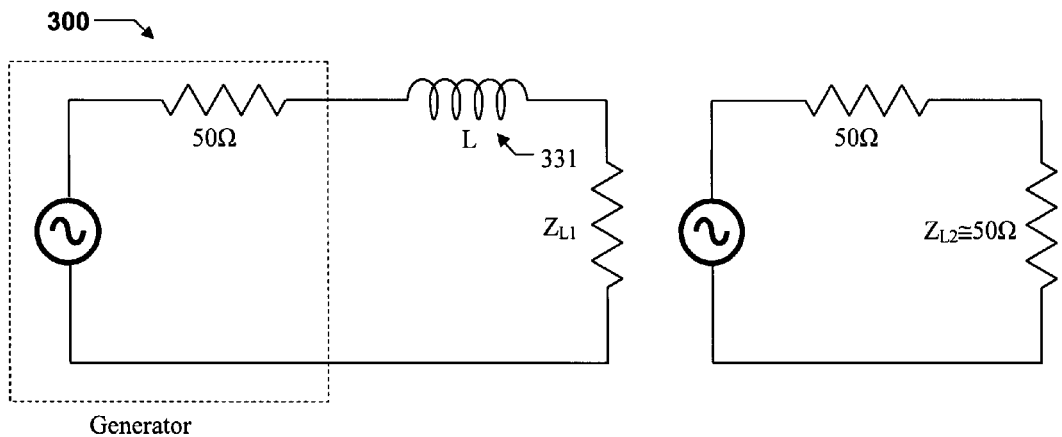
FIG. 4 is a schematic block diagram illustrating the components of a microwave ablation system of the present disclosure.
Figure 4:
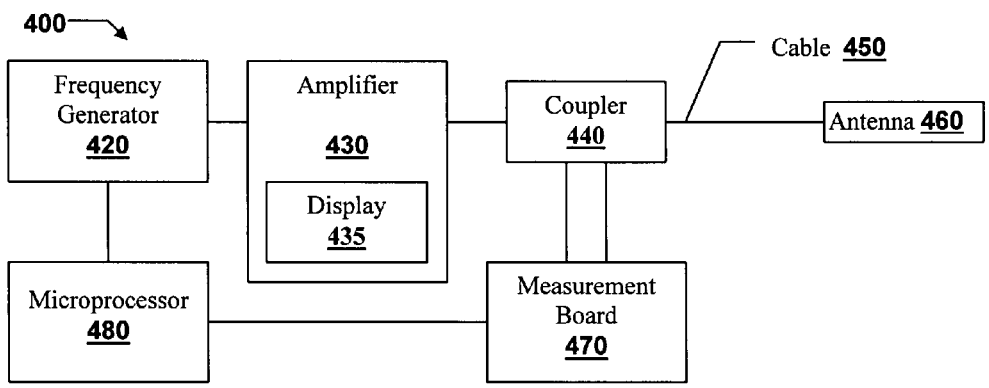

In accordance with the present disclosure, a second method of matching the impedance of the microwave probe 110 to the source impedance is referred to as "frequency tuning." As seen in FIG. 4, a schematic illustration depicts a microwave ablation system 400 that may be used for frequency tuning.

Microwave ablation system 400 includes a transmission line including a microwave frequency generator 420, an amplifier 430 electrically coupled to generator 420, a monitor such as coupler 440 electrically connected to amplifier 430, and a microwave energy delivery device or antenna 460 electrically coupled to 440 via a transmission cable 450. Microwave ablation system 400 further includes a measurement board 470 electrically coupled to coupler 440 and a microprocessor 480 in a communication line connecting the measurement board 470 with the frequency generator 420.

Frequency generator 420 may take any suitable form and should be configured to adjust the frequency of the output signal. The optimal frequencies for microwave tissue ablation are generally in the neighborhood of those frequencies best suited for heating water. By way of example, frequency generator 420 may be capable of producing output frequencies in the range of about 850 MHz to about 1.35 GHz, although higher frequencies are contemplated by the present disclosure. Amplifier 430 should be capable of amplifying the relatively low energy signal generated by frequency generator 420. Amplifier 430 should also be capable of communicating information about both the forward power and any reflected power signals present in system 400. Amplifier 430 may include a 300 Watt amplifier operating in the frequency range of 800 to 1000 MHz. Coupler 440 should be capable of sampling forward power from amplifier 430 and also the power reflected by the targeted tissue. Coupler 440 may include a 40 dB dual directional coupler having operating parameters suitable for use in this application. Measurement board 470 is in communication with coupler 450 and is capable of monitoring forward and reflected power signals and/or communicating impedance measurements.

Cable 450 and antenna 460 may take any suitable form for use in a frequency tuning application. Here it is contemplated that the coaxial cable 254 and microwave probe 110 discussed with reference to FIG. 1 above may be used as cable 450 and antenna 460, respectively. Cable 450 may be selected to provide sufficient flexibility to allow antenna probe 110 to be conveniently positioned, and may also be selected to minimize power losses therethrough.

Figure 5:
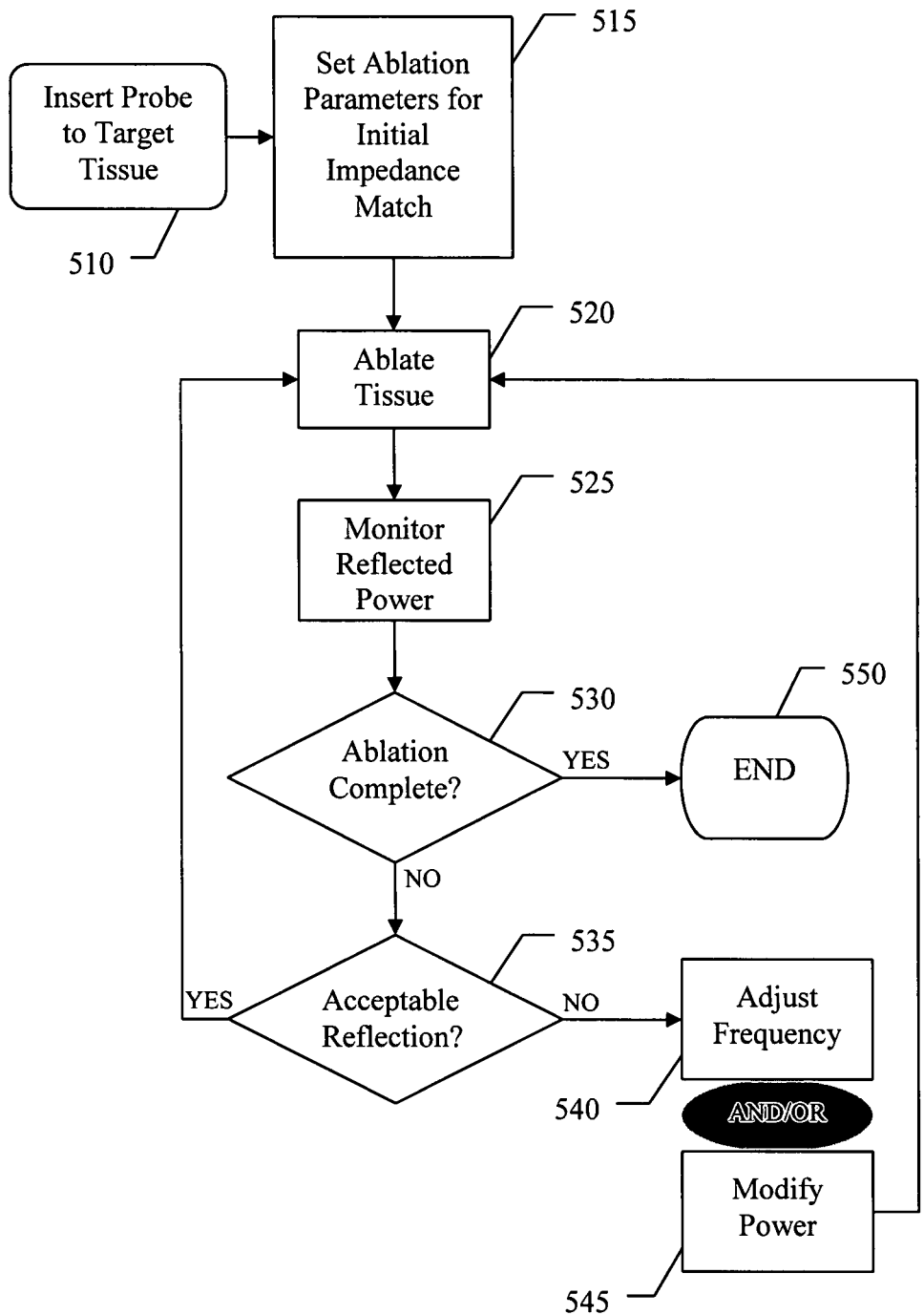
FIG. 5 is a flow diagram illustrating a method, according to the present disclosure, of using frequency tuning in an ablation cycle for impedance matching.

Turning now to FIG. 5, a flow diagram of a method of performing a tissue ablation in accordance with the present disclosure is shown. In accordance with the present disclosure, a microwave probe 110 may be directly inserted into the target tissue in accordance with any suitable method known in the art (Process 510). Insertion of microwave probe 110 to a depth of about 5.5 to about 6 cm or any other suitable depth may be appropriate. Next, an initial impedance match is made by adjusting the output frequency of generator 420 to effect a source impedance of about 50 ohms, the approximate impedance of the target tissue (Process 515). Amplifier 430 may be set according to the preference of a clinician or in one embodiment, to output from about 30 Watts to about 45 Watts. At such a setting, the target tissue will begin to ablate due to the delivery of microwave energy thereto via antenna 460 (Process 520). The forward power at antenna 460 may be calculated by applying a correction factor based on the energy expected to be lost in the cable 450 to the output power of the amplifier 430.

The cable loss is partly a function of the characteristics of cable 450 (e.g., length diameter, materials of construction, etc.) and the frequency of the energy delivered therethrough. The cable loss may be readily calculated from such known characteristics. After a predetermined amount of time, an indication of the power reflected (i.e. not delivered to the target tissue) may be communicated through amplifier 430 to the operator by a display 435 on the amplifier 430 (Process 525). The correction factor determined for the cable loss may be applied to the value displayed for the reflected power at the amplifier 430 to determine the amount of energy reflected at the antenna 460.

A large reflected power, at antenna 460 in relation to the forward power at antenna 460, is representative of a substantial impedance mismatch. Conversely, smaller reflections are characteristic of having achieved a matched impedance between the target tissue and the load source or between the reflected power and the forward power. Some reflected power may be acceptable and thus not require any adjustments to the frequency output by generator 420 (Decision 535).

During operation, if some threshold value of reflected power is exceeded (Decision 535), the output frequency of generator 420 may be adjusted (upwardly or downwardly) to reduce the reflected power to a level below the threshold value (Process 540). This frequency adjustment may be accompanied by an adjustment to the output power of amplifier 430 if it is deemed necessary in order to deliver the necessary power to the target tissue (Process 545).

Even a single adjustment to the frequency of the output signal of generator 420 during the ablation procedure may have a substantial or significant effect on the effectiveness of the ablation procedure. In some embodiment, microwave ablation system 400 may include, for example, a microcontroller 480 capable of automatically making many frequency adjustments during a given period of time. The ablation cycle may continue, continuously monitoring the reflected power and making frequency adjustments as necessary, until the target tissue has been sufficiently ablated (Decision 530). When the tissue has been sufficiently ablated, energy delivery to the tissue may cease (Process 550).

An ablation procedure performed on cow liver tissue yielded the exemplary values presented in Table 1 below. Initially the output frequency of generator 420 was set at 925 MHz, and the amplifier 430 was set to output 31 Watts. The output power from the amplifier was transmitted through a cable 450 known to have a loss of 1.25 dB. A cable loss (dB) is related to a correction factor (P) by the equation dB=10(log P). A correction factor of about 1.33 was thus determined for the cable 450. Dividing the 31 Watt output power of the amplifier 430 by the 1.33 correction factor yielded the initial value recorded for the load power. This initial value of 23.25 Watts represents the power delivered to the cow liver tissue load or the output power of the amplifier 430 less the power lost in the cable 450.

After the initial value of load power was thus calculated, subsequent values recorded for load power were based on a value recorded for the power reflected by the tissue. The values for power reflected were observed on the display 435 of amplifier 430 and thus represent the power reflected by the tissue load not lost in the cable 450 as the signal returned from the tissue to the amplifier 430. To determine the amount of power actually reflected by the tissue, the 1.33 correction factor was multiplied by the power reflected and recorded as the corrected power reflected. The values listed for load power subsequent to the initial value were calculated by subtracting the corrected power reflected from the initial load power calculated. The values for load power then represent the power delivered to the tissue and not reflected by the tissue. Initially the power reflected was recorded as Low because the power reflected was below the range detectable by the amplifier 430. Whenever possible, an impedance reading was recorded as illustrated in Table 1 below. Impedance readings may be used to determine a frequency needed for tuning.

TABLE 1

| Time (minutes) | Frequency (MHz) | Power Reflected (Watts) | Corrected Power Reflected (Watts) | Load Power (Watts) | Impedance (ohms) |
| --- | --- | --- | --- | --- | --- |
| 0.0 | 925 | Low | N/A | 23.25 | 43 + j8 |
| 0.5 | 925 | Low | N/A | 23.25 | 43 + j0 |
| 1.0 | 925 | Low | N/A | 23.25 | 43 − j2 |
| 1.5 | 930 | Low | N/A | 23.25 | — |
| 2.0 | 935 | Low | N/A | 23.25 | — |
| 2.5 | 940 | 0.6 | 0.8 | 22.45 | — |
| 3.0 | 940 | 0.6 | 0.8 | 22.45 | 33 − j12 |
| 3.5 | 940 | 0.7 | .93 | 22.32 | 33 − j12.9 |

TABLE 1-continued

| Time (minutes) | Frequency (MHz) | Power Reflected (Watts) | Corrected Power Reflected (Watts) | Load Power (Watts) | Impedance (ohms) |
|---|---|---|---|---|---|
| 4.0 | 940 | 0.7 | .93 | 22.32 | 33.5 − j14 |
| 4.5 | 940 | 0.7 | .93 | 22.32 | 33.6 − j14 |
| 5.0 | 940 | 0.85 | 1.13 | 22.12 | 33.4 − j17.7 |
| 5.5 | 940 | 1.0 | 1.33 | 21.92 | — |
| 6.0 | 940 | 1.8 | 2.4 | 20.85 | — |
| 6.5 | 940 | 2.0 | 2.66 | 20.59 | — |
| 7.0 | 940 | 2.2 | 2.93 | 20.32 | — |
| 7.5 | 940 | 2.8 | 3.72 | 19.53 | 33 − j39 |
| 8.0 | 940 | 3.2 | 4.3 | 18.95 | 33 − j42 |
| 8.5 | 940 | 3.5 | 4.7 | 18.55 | 33 − j43 |
| 9.0 | 940 | 3.5 | 4.7 | 18.55 | 33 − j44 |
| 9.5 | 940 | 4 | 5.32 | 17.93 | 33 − j46 |
| 10.0 | 940 | 4 | 5.32 | 17.93 | 33 − j48 |

As can be seen in Table 1, the power reflected by the tissue generally increased over time as the tissue was heated, just as expected. The output frequency of generator 420 was adjusted to 930 MHz after 1.5 minutes, to 935 MHz after 2 minutes, and 940 MHz after 2.5 minutes of the ablation procedure. These adjustments yielded a reflected power of 4 Watts after 10 minutes. With no frequency adjustments, a max reflected power of about 8 Watts could be expected around 10 minutes. Thus, a comparison of these reflected power values demonstrates the effect of frequency adjustments on the delivery of energy to the tissue.

Although the foregoing disclosure has been described in some detail by way of illustration and example, for purposes of clarity or understanding, it will be obvious that certain changes and modifications may be practiced within the scope of the appended claims.

What is claimed is:

1. A system for tissue ablation, comprising:
   a microwave antenna configured for direct insertion into a targeted tissue;
   a microwave energy generator coupled to the microwave antenna and configured to provide microwave energy of a predetermined frequency and having a generator impedance;
   an input line for receiving at least one of an output signal and microwave energy from the microwave energy generator;
   an output line for transmitting at least one of an impedance matched output signal and microwave energy to the microwave antenna; and
   an active matching network, including:
      a fixed inductor electrically connected in series between the input line and the output line;
      a first capacitor and a first tuning diode electrically connected in series to one another and connected to the input line at a location upstream of the fixed inductor;
      a second capacitor and a second tuning diode electrically connected in series to one another and connected to the output line at a location downstream of the fixed inductor;
      a first inductor connected to a first direct current source via a first supply line and connected at a point between the first capacitor and the first tuning diode; and a second inductor connected to a second direct current source via a second supply line and connected at a point between the second capacitor and the second tuning diode,
      wherein the first and second tuning diodes are selectively switchable from an off state to an on state to place at least one of the first capacitor and second capacitor in an active state with the fixed inductor to compensate for a difference between the generator impedance and an impedance of the targeted tissue.

2. The system of claim 1, wherein an anode of the second tuning diode is grounded.

3. The system of claim 1, wherein an anode of the first tuning diode is grounded.

4. The system of claim 1, wherein the first and second tuning diodes are varactor diodes usable such that when a direct current voltage is respectively applied on the first and second supply lines, a capacitance exhibited by each of the varactor diodes will vary in accordance with the direct current voltage applied thereto.

5. The system of claim 4, wherein the first and second inductors are selected to have sufficiently high impedances over an appropriate range of frequencies so that the first and second inductors act as RF chokes, thereby keeping the first and second supply lines free from an alternating current supplied to the output line.

6. The system of claim 1, wherein the first tuning diode is a PIN diode.

7. The system of claim 1, wherein the second tuning diode is a PIN diode.

8. A system for tissue ablation, comprising:
   a microwave energy generator configured to provide microwave energy of a predetermined frequency and having a generator impedance;
   a microwave antenna operably coupled to the microwave energy generator;
   an input line for receiving at least one of an output signal and microwave energy from the microwave energy generator;
   an output line for transmitting at least one of an impedance matched output signal and microwave energy to the microwave antenna; and
   an active matching network, including:
      a fixed inductor electrically connected in series between the input line and the output line;
      a first capacitor and a first tuning diode electrically connected in series to one another and connected to the input line at a location upstream of the fixed inductor;
      a second capacitor and a second tuning diode electrically connected in series to one another and connected to the output line at a location downstream of the fixed inductor;
      a first inductor connected to a first direct current source via a first supply line and connected at a point between the first capacitor and the first tuning diode; and a second inductor connected to a second direct current source via a second supply line and connected at a point between the second capacitor and the second tuning diode, wherein the active matching network is configured to selectively switch off at least one of the first tuning diode by adjusting the direct current supplied via the first supply line and the second tuning diode by adjusting direct current supplied via the second supply line, in order to have either the first capacitor or the second capacitor active with the fixed inductor to compensate for a difference between the generator impedance and an impedance of the targeted tissue.

9. The system of claim 8, wherein an anode of the first tuning diode is grounded.

10. The system of claim 8, wherein an anode of second tuning diode is grounded.

11. The system of claim 8, wherein the first tuning diode is a PIN diode.

12. The system of claim 8, wherein the second tuning diode is a PIN diode.

13. A system for tissue ablation, comprising:
- a microwave antenna configured for direct insertion into a targeted tissue;
- a transmission line;
- a microwave energy generator coupled to the microwave antenna by the transmission line and configured to adjust a frequency of microwave energy generated thereby and having a generator impedance;
- a monitor coupled to the transmission line capable of measuring a reflected power signal during operation of the microwave antenna;
- a communication line configured to communicatively couple the monitor and the microwave energy generator; and
- an active matching network coupled to the transmission line, wherein the active matching network circuit includes:
  - an input line for receiving an output signal or microwave energy from the microwave energy generator;
  - an output line for transmitting an impedance matched output signal or microwave energy to the microwave antenna;
  - a fixed inductor electrically connected in series between the input line and the output line;
  - a first capacitor and a first tuning diode electrically connected in series to one another and connected to the input line at a location upstream of the fixed inductor;
  - a second capacitor and a second tuning diode electrically connected in series to one another and connected to the output line at a location downstream of the fixed inductor;
  - a first inductor connected to a first direct current source via a first supply line and connected in series between the first capacitor and the first tuning diode, and a second inductor connected to a second direct current source via a second supply line and connected to the second capacitor and the second tuning diode,
  wherein the first and second tuning diodes are adjustable in order to match an impedance of a load on the output line to that of the microwave antenna, such that direct current voltage is applied on the first and second supply lines to tune the first and second tuning diodes to create a substantial match between the generator impedance and an equivalent impedance of the targeted tissue.

* * * * *